(12) United States Patent
Nilsson

(10) Patent No.: US 8,153,008 B2
(45) Date of Patent: Apr. 10, 2012

(54) DEVICE AND METHOD FOR FILTERING BLOOD

(75) Inventor: Anders Nilsson, Vasteras (SE)

(73) Assignee: Gambro Lundia AB, Lakewood, CO (US)

( * ) Notice: Subject to any disclaimer, the term of this patent is extended or adjusted under 35 U.S.C. 154(b) by 425 days.

(21) Appl. No.: 10/514,634

(22) PCT Filed: May 14, 2003

(86) PCT No.: PCT/SE03/00783
§ 371 (c)(1),
(2), (4) Date: Feb. 17, 2005

(87) PCT Pub. No.: WO03/097130
PCT Pub. Date: Nov. 27, 2003

(65) Prior Publication Data
US 2005/0126962 A1    Jun. 16, 2005

(30) Foreign Application Priority Data
May 17, 2002 (SE) ...................................... 0201496

(51) Int. Cl.
*B01D 61/00* (2006.01)
*B01D 37/00* (2006.01)
*B01D 27/00* (2006.01)
*B01D 27/08* (2006.01)
*B01D 29/00* (2006.01)
*B01D 35/00* (2006.01)

(52) U.S. Cl. ..... 210/650; 210/109; 210/114; 210/195.2; 210/252; 210/256; 210/257.1; 210/257.2; 210/321.6; 210/321.65; 210/321.79; 210/321.8; 210/321.87; 210/321.88; 210/321.89; 210/433.1; 210/436; 210/472; 210/473; 210/477; 604/4.01; 604/5.01; 604/6.09; 604/6.15; 604/404; 604/403; 604/405; 604/408

(58) Field of Classification Search ................... 210/645, 210/646, 650, 651, 109, 114, 195.2, 252, 210/256, 257.1, 257.2, 321.6, 321.65, 321.78, 210/321.79, 321.8, 321.87, 321.88, 321.89, 210/433.1, 436, 472, 473, 477; 422/44; 604/4.01, 604/5.01, 6.09, 6.15, 403, 404, 405, 408
See application file for complete search history.

(56) References Cited

U.S. PATENT DOCUMENTS
3,388,803 A * 6/1968 Scott ........................ 210/321.78
(Continued)

FOREIGN PATENT DOCUMENTS
EP            0274178          7/1988
(Continued)

OTHER PUBLICATIONS
Japanese Office Action dated Apr. 24, 2009 (in Japanese and English).

*Primary Examiner* — John Kim
(74) *Attorney, Agent, or Firm* — Jacobson Holman PLLC

(57) ABSTRACT

Device (5) for filtering blood including a filter unit (7) having a blood filter, an inlet (8) for blood to be filtered and being connectable to an artery of a patient and a blood outlet (9) for filtered blood and being connectable to a vein of the patient, and having a filtrate container (6,14), that encloses the filter unit (7), for receiving filtrate (12) passing through the blood filter during a filtering process and that the filtrate container (6,14) is a closed container, which in a filled state is arranged to establish a counter-pressure over the blood filter, whereby the filtering process is interrupted. The invention also concerns a system including the above device.

13 Claims, 2 Drawing Sheets

U.S. PATENT DOCUMENTS

| | | | |
|---|---|---|---|
| 3,884,808 A * | 5/1975 | Scott | 210/109 |
| 4,071,444 A * | 1/1978 | Ash et al. | 210/637 |
| 4,235,233 A | 11/1980 | Mouwen | 128/214 |
| 4,275,732 A | 6/1981 | Gereg | 128/276 |
| 4,765,907 A * | 8/1988 | Scott | 210/648 |
| 5,284,470 A * | 2/1994 | Beltz | 604/4.01 |
| 5,993,657 A | 11/1999 | Williams et al. | 210/321 |
| 6,579,265 B1 * | 6/2003 | Kihara et al. | 604/174 |

FOREIGN PATENT DOCUMENTS

| | | |
|---|---|---|
| GB | 2052948 | 2/1981 |
| JP | 58-75558 | 5/1983 |
| JP | 2001-520092 | 10/2001 |
| WO | WO95/29731 | 11/1995 |

* cited by examiner

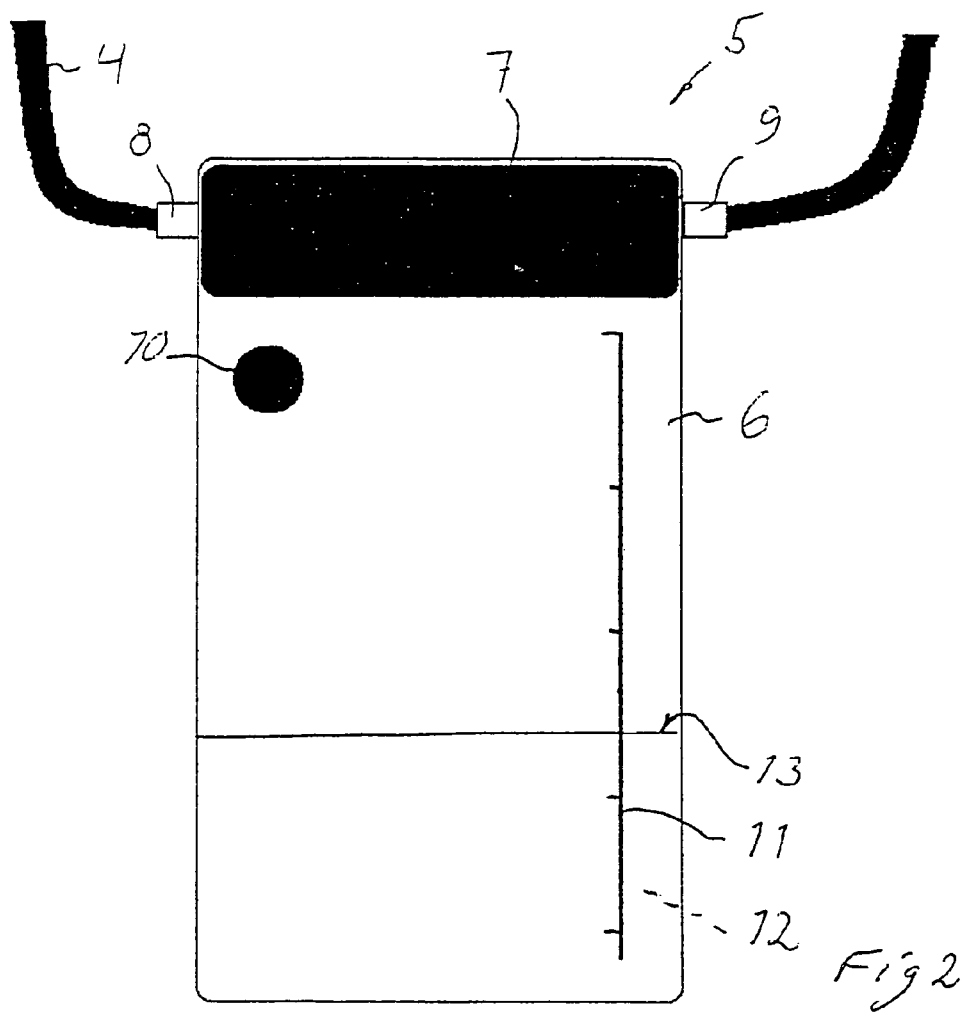

DEVICE AND METHOD FOR FILTERING BLOOD

This is a nationalization of PCT/SE03/00783 filed May 14, 2003 and published in English.

FIELD OF THE INVENTION

The invention concerns a device for filtering blood. The invention also concerns a system for ultra filtration of blood including such a device.

DESCRIPTION OF PRIOR ART

It is previously known to treat patients having chronic renal failure with hemodialysis. Hemodialysis treatments are traditionally carried out about three times a week, whereby the blood is purified and the liquid balance is adjusted at a hemodialysis site in a hospital.

One condition for hemodialysis is the establishment of a connection to the patient's bloodstream having a sufficience flow. This may be accomplished by inserting catheters into the blood system or to use-an implanted bloodstream access device which may be connected to an artificial kidney. Such devices may be used repeatedly for numerous treatments.

Since the kidneys of a patient suffering from renal conditions usually do not produce any urine, the patient normally turns up at the hemodialysis site with an excess of liquid in the body. After the hemodialysis treatment this has been changed to a shortage of liquid in the body. These fluctuating fluid levels may cause serious health problems besides the conditions that the patients are treated for.

AIM AND MOST IMPORTANT FEATURES OF THE INVENTION

It is an aim of this invention to provide a solution to the above problem and in particular to suggest a simple, economic and effective solution allowing better control of the liquid balance for dialysis patients having a chronic renal failure diagnosis.

The aim is achieved with a device for filtering blood including a filter unit having a blood filter, an inlet for blood to be filtered and being connectable to an artery of a patient and a blood outlet for filtered blood and being connectable to a vein of the patient, and having a filtrate container for receiving filtrate passing through the blood filter during a filtering process and that the filtrate container is a closed container which in a filled state is arranged to establish a counter-pressure over the blood filter, whereby the filtering process is interrupted characterized in that the filtrate container encloses the filter unit.

This way it is possible to effectively filter out a desired, predetermined amount of liquid from the blood of the patient between the ordinary hemodialysis treatments. This brings about great advantages for the patients, since it provides important opportunities to better control the liquid balance between the treatments, whereby the liquid level is allowed to be equalised over time. This measure can radically r educe strain on the patient's body caused by fluctuating liquid levels.

The device is simple to make portable so as to be capable of being conveniently used outside a dialysis site. Patients could therefore without any difficulty be trained to use it, for example, in the homes, and still be movable. This allows the patients to attend also to other tasks, such as cooking, cleaning etc., without being restricted to stay in bed or be tied to a specific, stationary apparatus for a substantial time during the treatment. In particular, the provision of a filtrate container which encloses the filter unit simplifies production and handling of the device as well as the process for its use in practice.

Providing a substantially rigid vessel for collecting filtrate and having an air vent therein, allows production and provision of a robust device which can be easily handled in virtually any environment.

Providing a flexible expandable container, which is collapsible in an empty state, as the filtrate container, simplifies transport; storage and related handling.

Production, handling and use is further enhanced when the device comprises an integral unit which is being disposable after use.

Further advantages are obtained with other aspects of the invention. Such aspects are subject to dependent claims and will become apparent from the following description of embodiments.

BRIEF DESCRIPTION OF THE DRAWINGS

The invention is now described in greater detail at the background of an embodiment and with reference to the annexed drawings, wherein:

FIG. 2 shows a device for filtering blood included in the system of FIG. 1, and

FIGS. 3 and 4 show alternative embodiments of the device according to the invention.

DESCRIPTION OF A PREFERRED EMBODIMENT

Figure 1:
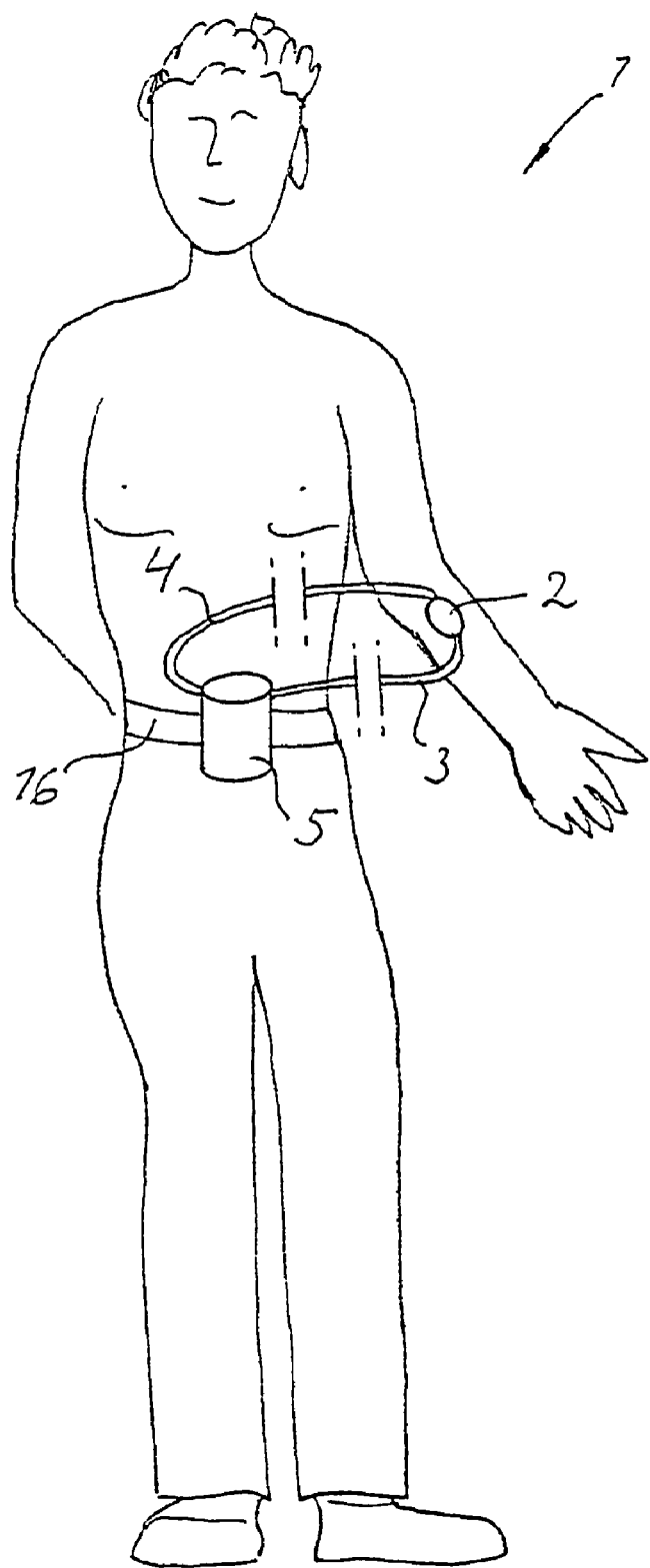
FIG. 1 shows a system according to the invention carried by a patient.

In FIG. 1 a dialysis patient 1 suffering from renal failure conditions carries an implanted bloodstream access device 2 which is connected over connection houses 3, 4 to a blood filtering device 5. The bloodstream access device 2 is preferably an implanted device, as the one disclosed in WO 99/20338 (Danielson et. al.).

Such an access device is marketed under the trade mark Hemaport® 605. That device provides a considerable pressure difference between the artery and the vein side so as to drive a continuous flow of blood through an external circuit. Also other blood access devices providing sufficient pressure difference may be used together with the invention.

In this connection it could be mentioned that vascular grafts and fistulas which are commonly used for gaining access to a patient's bloodstream do not provide sufficient pressure difference for driving the blood through a blood filtering device according to the invention.

In the case illustrated in FIG. 1, the blood filtering device includes a rigid container which is carried by the patient 1 with the aid of a fastening strap 16.

The blood filtering device 5 is shown in greater detail in FIG. 2. Here the device 5 is shown including a filtrate container 6 which at its upper portion contains a filter unit 7. The filter unit is comprised of a substantially tubular, hollow ultra filtration filter having closed ends in inlet and outlet regions of the filter unit 7. An inlet connection hose 4 is connected to an inlet nipple 8 leading in to the interior of the filter unit 7.

At the outlet end of the filter unit 7, an outlet nipple 9 connects with an outlet connection hose 3. The inlet and outlet connection hoses 4 and 3 are connected to the respective artery and vein side of the bloodstream access device 2 (FIG. 1). The inlet and outlet nipples 8, 9 also contribute to positioning the filter unit 7 with respect to the filtrate container 6 by being engaged in through-holes (not shown) in the wall of the container.

In use of the device 5, blood flows from inlet nipple 8 through the filter unit 7, where a portion of the liquid component of the blood is filtered out as filtrate through the filter wall of the filter unit 7 so as to be collected inside the filtrate container 6. The remaining components of the blood are discharged through the outlet nipple 9 over the connection hose 3 so as to be brought back into the bloodstream of the patient over the bloodstream access device 2 (FIG. 1).

The properties of the filter of the filter unit 7 is chosen in such a way that an appropriate amount of said liquid component is filtered out as filtrate. This could be easily tested for for example ultra filtration filters and choosing a suitable filter area for chosen material properties so as to apply to certain conditions and applications of use. One example of a condition to consider is the body weight of a patient.

In case the filtrate container 6 is a rigid or semi-rigid container, gas or air being present inside the filtrate container must be allowed to escape therefrom so as to leave room for the filtrate. For that reason at least one air vent 10 is provided at an appropriate position at the top region of the filtrate container 6.

Preferably the air vent 10 includes a membrane which is air or gas permeable and liquid impermeable so that no liquid leakage will occur through the air vent 10 while gas may escape. Other solutions such as liquid controlled flap-valves or the like are also possible to use, in order to allow air to escape from the filtrate container but liquid to remain inside.

The filtrate container 6 may come in different volumes, for example having between 0.2 to 1 liter volume, depending on such conditions as for example body weight of the patient and also which amount of liquid that is desired to withdraw from the patient at the specific occasion.

Preferably the filtrate container 6 is at least translucent, allowing a visual indication of the level 13 of filtrate 12 inside the container. The container may also have a scale 11 readable against the filtrate level 13.

According to the invention, when a desired amount of filtrate is withdrawn from the bloodstream the filtrate container 6 will be completely filled with that amount of filtrate. This will result in that the filtering operation of the filter unit 7 is interrupted because a counter-pressure will be established over the filter wall of the filter unit. This in turn results in that all blood entering the filter unit 7 through the inlet nipple also will flow through the outlet nipple 9. From there it will be fed back into the bloodstream through the outlet connection hose 3 and the bloodstream access device 2 (FIG. 1).

As an alternative, it is possible that a counter-pressure over the blood filter will be established when the filtrate 12 reaches a filtrate level over the air vent 10, thereby trapping air between the filtrate level 13 and the filter unit 7. This may create a sufficient counter-pressure over the wall of the filter for the filter action be terminated.

In FIG. 3 a filtrate container 14 is shown being a flexible, collapsible pouch type filtrate container. In this case a counter-pressure of a magnitude being sufficient for the filter action to be terminated will be established when the pouch comprising the filtrate container 14 reaches such an expanded state that further expansion is impossible with the pressure available through the wall of the filter unit 7. Also in this case the filter unit is placed inside the filtrate container 14.

FIG. 4 shows a further embodiment, wherein a filtrate container 14, substantially like the one described in connection with FIG. 3, is contained inside a rigid outer container 15. That outer container 15 must not be liquid tight but may only be intended to protect the flexible container and possibly to provide a volume restriction thereof.

It is highly preferred that all parts of the system for blood filtering are disposable after use, including the filtrate container, the filter unit, the connection hoses and also a connection lid which is intended to co-operate with the blood-stream access device 2 (FIG. 1). Such a connection lid may be of a kind described in the above mentioned WO 99/20338.

Materials for use in elements comprising the invention must fulfil normal requirements for medical purposes. Filter materials for use in the filter units shall be of the kind normally used for filtration of blood such as ultra filtration filters.

The invention is described for filtering a liquid component from a patient's blood. That liquid component may, however, include also certain solid substances.

The invention claimed is:

1. A device for filtering blood comprising:
   a filter unit in connection with an inlet for blood to be filtered and being connectable to an artery of a patient through an inlet nipple and a blood outlet for filtered blood and being connectable to a vein of the patient through an outlet nipple, the filter unit further comprising closed ends in inlet and outlet regions of the filter unit which are connected to the inlet nipple and the outlet nipple, and
   a filtrate container for receiving filtrate passing through the filter unit during a filtering process, said filtrate container enclosing the filter unit,
   the filtrate container being a closed container and, in a filled state, the filtrate container establishes a counter-pressure over the filter unit so that the filtering process is interrupted,
   the filtrate container including a substantially rigid vessel for collecting filtrate and an air vent for allowing the escape of air from the vessel during a filtering process.

2. The device according to claim 1, wherein the air vent comprises an air permeable, liquid non-permeable membrane.

3. A method for filtering blood of a patient, said method comprising the steps of:
   providing a filter unit having an inlet and an outlet, and a filtrate container enclosing said filter unit in an upper portion of the filtrate container for receiving filtrate passing through the filter unit during a filtering process, wherein the filter unit further comprises closed ends in inlet and outlet regions of the filter unit which are connected to an inlet nipple and an outlet nipple;
   connecting the filter unit inlet to an artery of the patient and the filter unit outlet to a vein of the patient;
   providing sufficient pressure difference for driving a portion of a liquid component of the blood through the filter unit to form a filtrate;
   collecting the filtrate in at least a lower portion of the filtrate container;
   discharging remaining components of the blood via the filter unit outlet; and
   interrupting or stopping the filtering process when a counter pressure over the filter unit is established in the filtrate container.

4. A method for filtering blood of a patient, said method comprising the steps of:
   providing a filter unit having an inlet and an outlet, and a filtrate container enclosing said filter unit for receiving filtrate passing through the filter unit during a filtering process, wherein the filter unit further comprises closed ends in inlet and outlet regions of the filter unit which are connected to an inlet nipple and an outlet nipple;

connecting the filter unit inlet to an artery of the patient and the filter unit outlet to a vein of the patient;

providing sufficient pressure difference for driving a portion of a liquid component of the blood through the filter unit to form a filtrate;

collecting the filtrate in the filtrate container;

discharging remaining components of the blood via the filter unit outlet; and interrupting or stopping the filtering process when a counter pressure over the filter unit is established in the filtrate container, the filtrate container including a substantially rigid vessel for collecting filtrate and an air vent for allowing the escape of air from the vessel during the filtering process.

5. The method according to claim 4, wherein the air vent comprises an air permeable, liquid non-permeable membrane.

6. The method according to claim 3, wherein the filtrate container includes a flexible and expandable container that is collapsed in an empty state.

7. The method according to claim 6, wherein the flexible and expandable container is enclosed in a substantially rigid outer container.

8. The method according to claim 3, wherein the filter unit comprises a substantially tubular filter body.

9. The method according to claim 3, wherein the filter unit is an ultra filtration filter.

10. The method according to claim 3, wherein the filtrate container has a filtration volume of about 0.2-1 liter.

11. The method according to claim 3, wherein an implanted bloodstream access device is provided for connecting with said inlet and outlet of the filter unit.

12. The method according to claim 9, wherein the above steps are performed to partially replace a hemodialysis treatment.

13. A method for filtering blood of a patient, said method comprising the steps of:

providing a filter unit having an inlet with an inlet nipple and an outlet with an outlet nipple, and a closed filtrate container enclosing said filter unit for receiving filtrate passing through the filter unit during a filtering process, wherein the filter unit further comprises closed ends in inlet and outlet regions of the filter unit which are connected to the inlet nipple and the outlet nipple;

connecting the filter unit inlet to an artery of the patient and the filter unit outlet to a vein of the patient;

providing sufficient pressure difference in the filter unit for driving a portion of a liquid component of the blood through the filter unit to form a filtrate;

collecting the filtrate in the closed filtrate container;

discharging remaining components of the blood via the filter unit outlet; and interrupting the filtering process through the filter unit when a counter pressure over the filter unit is established in the filtrate container.

\* \* \* \* \*